United States Patent [19]

Winston et al.

[11] Patent Number: 4,943,429

[45] Date of Patent: Jul. 24, 1990

[54] DENTIFRICE GELS CONTAINING SODIUM BICARBONATE

[75] Inventors: Anthony E. Winston, East Brunswick; Regina M. Miskewitz, Hillsborough, both of N.J.

[73] Assignee: Church & Dwight Co., Inc., Princeton, N.J.

[21] Appl. No.: 197,218

[22] Filed: May 23, 1988

[51] Int. Cl.$^5$ .......................... A61K 7/16; A61K 7/18
[52] U.S. Cl. .......................................... 424/52; 424/49
[58] Field of Search ........................ 424/49, 58, 52

[56] References Cited

U.S. PATENT DOCUMENTS

| | | |
|---|---|---|
| 2,128,917 | 9/1938 | Crocker . |
| 3,906,090 | 9/1975 | Colodney . |
| 3,927,202 | 12/1975 | Harvey et al. . |
| 3,935,305 | 1/1976 | Delaney et al. . |
| 3,937,321 | 2/1976 | Delaney et al. . |
| 3,937,803 | 2/1976 | Delaney et al. ........................ 424/49 |
| 3,937,804 | 2/1976 | Delaney et al. . |
| 3,943,240 | 3/1976 | Delaney et al. . |
| 3,985,668 | 10/1976 | Hartman ............................... 252/99 |
| 4,005,027 | 1/1977 | Hartman ............................... 252/95 |
| 4,036,949 | 7/1977 | Colodney . |
| 4,051,055 | 9/1977 | Trinh et al. ........................... 252/95 |
| 4,051,056 | 9/1977 | Hartman ............................... 252/99 |
| 4,123,395 | 10/1978 | Maguire et al. ..................... 252/559 |
| 4,160,022 | 7/1979 | Delaney et al. . |
| 4,273,759 | 6/1981 | Gaffar et al. . |
| 4,397,755 | 8/1983 | Brierley et al. ..................... 252/113 |
| 4,487,757 | 12/1984 | Kozpeoplou ......................... 424/49 |
| 4,528,180 | 7/1985 | Schaeffer ............................. 424/53 |
| 4,547,362 | 10/1985 | Winston et al. ..................... 424/49 |
| 4,590,065 | 5/1986 | Piechota, Jr. et al. . |
| 4,623,536 | 11/1986 | Winston et al. ..................... 424/49 |
| 4,647,451 | 3/1987 | Piechota .............................. 424/49 |
| 4,663,153 | 5/1987 | Winston et al. . |
| 4,687,663 | 8/1987 | Schaeffer ............................. 424/53 |
| 4,721,614 | 1/1988 | Winston et al. . |
| 4,776,500 | 10/1988 | Ford ................................. 424/53 X |
| 4,784,788 | 11/1988 | Lanez ................................. 252/114 |
| 4,788,052 | 11/1988 | Ng et al. .............................. 424/53 |

*Primary Examiner*—Shep K. Rose
*Attorney, Agent, or Firm*—Bryan, Cave, McPheeters & McRoberts

[57] ABSTRACT

A sodium bicarbonate-based dentifrice gel which comprises sodium bicarbonate in an aqueous carrier with a humectant such as glycerol or sorbitol. Secondary abrasives such as hydrogen silica gels may be incorporated in the dentifrice gel.

12 Claims, No Drawings

DENTIFRICE GELS CONTAINING SODIUM BICARBONATE

TECHNICAL FIELD

This invention relates to dentifrice gels, viz., translucent (i.e., visually clear or partially clear) dentifrice formulations, as distinguished from opaque toothpastes, containing sodium bicarbonate.

BACKGROUND OF THE INVENTION

Many different dentifrice compositions are known for cleaning, whitening, and preserving the teeth. Of these known dentifrices, many include water-insoluble abrasives such as calcium carbonate, dicalcium phosphate, tricalcium phosphate, calcium pyrophosphate, sodium metaphosphate, or corresponding magnesium salts, which act as polishing agents for the teeth. Conventional cream or paste dentifrices containing such abrasives are opaque.

Since the ultimate goal of any oral hygiene regimen is preservation of the teeth, it is widely accepted that dentifrice compositions should include polishing agents having the minimum abrasivity consistent with good cleaning characteristics. Sodium bicarbonate is a desirable abrasive from this standpoint since it is low in abrasion and imparts an exceptionally clean, fresh feel to the mouth. Sodium bicarbonate particles are relatively soft as compared to most conventional abrasive materials used in dentifrice compositions. Thus, the American Dental Association has recommended that if only a slight degree of abrasion is necessary to keep teeth from staining, baking soda is usually a satisfactory abrasive. *Accepted Dental Therapeutics*, pages 340–41 (38th Ed., 1979).

Sodium bicarbonate has, accordingly, previously been used as an abrasive in dentifrices. Thus, sodium bicarbonate has both been described in the literature as an ingredient of tooth powders (see Winston, et al, U.S. Pat. No. 4,547,362 and 4,663,153 owned by the assignee of the present invention) and toothpastes and dental creams (see Delaney, U.S. Pat. Nos. 3,935,305; 3,927,321; 3,937,803; 3,937,804; and 3,943,240; and Winston, et al, U.S. Pat. Nos. 4,623,536 and 4,721,614, owned by the assignee of the present invention); and has been incorporated in commercial tooth powders and toothpastes (ARM & HAMMER DENTAL CARE tooth powder and toothpaste, and COLGATE PEAK).

In recent years, gel dentifrices have gained substantial popularity in the dentifrice market. They provide a esthetic appeal which frequently connotes mouth freshening to the consumer. Such translucent gels are produced when the polishing agent or agents incorporated therein have substantially the same refractive index as the gel vehicle. See Colodney, U.S. Pat. Nos. 3,906,090 and 4,036,949, and Harrison U.S. Pat. No. 3,911,102. Typical of the abrasives which may be used in such gels are the hydrated silicas and the synthetic amorphous complex aluminosilicate salts of alkali metals or alkaline earth metals which have refractive indices of about 1.45–1.50.

Since the refractive index of water is only about 1.33, the liquid carriers for gel dentifrices generally contain humectants such as glycerin or sorbitol which have higher refractive indices (1.45–1.50) and which increase the refractive index of the carrier to about that of the polishing agent. One such dentifrice gel having a balanced refractive index is described in Harvey, et al, U.S. Pat. No. 3,927,202. Harvey discloses gels incorporating up to 50% of an alkali metal phosphate polishing agent having a refractive index between 1.435 and 1.465, in a vehicle comprising from 20% to 80% of a water-humectant mixture and from 0.5–10% of a gelling agent in proportions such that the vehicle has a refractive index of between 1.36 and 1.47. (Harvey, col. 1, lines 40–57).

Sodium bicarbonate has three indices of refraction (i.e., 1.376, 1.500, and 1.58; see Handbook of Chemistry and Physics, 66th Ed., CRC Press (1985)). These disparate indices differ so markedly that it is impossible to reasonably closely match the refractive indices thereof with any liquid carrier, in order to provide a translucent gel.

It is, accordingly, among the objects of the present invention to provide a sodium bicarbonate-based dentifrice gel which, notwithstanding differences in the refractive indices of the ingredients thereof, is nevertheless wholly or partially transparent. Other objects and advantages of the invention will be apparent from the following description of preferred embodiments thereof.

SUMMARY OF THE INVENTION

In accordance with the present invention, a dentifrice gel is provided comprising up to about 60% by weight and, preferably, about 5 to 35%, sodium bicarbonate, in an aqueous carrier containing at least about 22%, and preferably about 25 to 55%, of a humectant such as glycerol or sorbitol. When, on the other hand, the humectant is incorporated in amounts less than about 20%, translucent gels are not formed. The dentifrice gel formulation of the invention provides a cleaning and whitening agent having esthetic appeal. Also, the sodium bicarbonate dentifrice gel is an effective mouth freshener.

It has been found that the use of coarser grades of bicarbonate increases the clarity of the gel of this invention. The use of coarser grades becomes necessary when higher levels of sodium bicarbonate are employed in the product. When very fine grades of sodium bicarbonate are used, significantly less bicarbonate can be incorporated in the product without the loss of gel characteristics. When, for example, bicarbonate particles having a median particle size of less than about 44 microns (Grade 3DF) are incorporated in the dentifrice, gel formulations may be produced containing up to about 30% of the bicarbonate abrasive. Where, on the other hand, coarser bicarbonate particles having a median particle size of greater than about 149 microns (Grade 5) are incorporated, gels may be formed containing up to about 60% of the bicarbonate.

A further, and surprising, advantage of the gel of the invention is that secondary abrasives, such as the hydrous silica gels, may be incorporated in the gel in amounts of up to about 20% of the gel without materially affecting its clarity.

DETAILED DESCRIPTION OF THE INVENTION

The dentifrice gel of the present invention desirably includes the following ingredients:

| Ingredient | Percentage by Weight |
|---|---|
| Sodium bicarbonate | 5 to 60% |

| Ingredient | Percentage by Weight |
|---|---|
| (median particle size from 10 to 200 microns) | |
| Secondary abrasive | up to 20%, preferably from 5 to 15% |
| Humectant | 15 to 60% |
| Organic thickener | up to 3%, preferably from 0.1 to 1.0% |
| Inorganic gelling agent | up to 12%, preferably from 3 to 10% |
| Surfactant | up to 5%, preferably from 0.2 to 2.0% |
| Flavoring agent | up to 2%, preferably from 0.2 to 2.0% |
| Sweetener | up to 5%, preferably from 0.1 to 5% |
| Fluoridating agent | up to 3%, preferably to provide between 1000–2000 ppm fluoride ion |
| Water | up to 25%, preferably from 2 to 10% |

As indicated hereinabove, the amount of the sodium bicarbonate abrasive to be added to the dentifrice ge varies with the size of the bicarbonate particles used. Finer grades of sodium bicarbonate have the advantage of providing a smoother consistency to the gel. Coarser grades of sodium bicarbonate, however, allow higher levels of sodium bicarbonate to be included in the formulation while retaining the translucent characteristics of the dentifrice. With coarser bicarbonate abrasives, the resulting products have an interesting granular crystalline appearance. It is most preferred to incorporate sodium bicarbonate having a median particle size range of from about 74 to 149 microns, in amounts of from about 15 to 35% of the gel. On the other hand, when finer bicarbonate abrasives are utilized, e.g., having a median particle size of from about 44 to 74 microns (Grade 1), it is preferred to incorporate sodium bicarbonate in amounts of from about 5 to 30%. When coarser bicarbonate abrasives are used, e.g., having a median particle size in excess of 149 microns, preferred levels of sodium bicarbonate ar between 25–50% of the gel.

Since sodium bicarbonate is an especially mild abrasive, particularly at the levels incorporated in the dentifrice gels hereof, it is preferable to include a secondary abrasive in the dentifrice gel. It has been found that, when the primary bicarbonate abrasive is incorporated in the gel in the proportions described above, viz., in amounts of from about 15 to 35%, secondary abrasives of the type normally utilized in translucent dentifrice gels may also be incorporated in amounts of up to about 20% of the gel while still maintaining the optical clarity (translucency) thereof. Polishing agents so useful as secondary abrasives in the gels of the present invention include alkali metal phosphates and complex aluminosilicates such as described in the aforesaid U.S. Pat. Nos. 3,927,202; 3,906,090; 3,911,102; and 4,036,949; and, preferably, amorphous silica such as the hydrous silica gels (commercially available, for example, as Sylodent 700 and 756).

One of the advantages of the hydrous silica gels is that they allow significant flexibility in adjusting the abrasivity characteristics of the formulation by varying the type or level of hydrous silica gel used, as will be illustrated in some of the examples which follow.

As noted, the humectant (desirably glycerin or sorbitol, or mixtures thereof) is incorporated in an amount of at least about 15% of the dentifrice formulation in order to preserve the gel characteristics thereof. Low molecular weight polyethylene glycols and propylene glycols (e.g., having average molecular weights of about 300 to 600) may be substituted for all or part of the glycerin and/or sorbitol, while still retaining the gel characteristics imparted by the humectant component. It is particularly preferred to utilize from about 25 to 55% of the humectant when the bicarbonate is incorporated in the gel in an amount of about 15 to 35% thereof.

As shown in some of the examples which follow, we have found that one of the important factors controlling the clarity of the gel is the ratio of the humectant to water used in the formulation. In general, the higher the humectant to water ratio the clearer the gel. Also, formulations containing sorbitol can tolerate more water than formulations containing glycerol while maintaining their clarity. For glycerol, the preferred ratio of humectant to water is greater than about 1:1, preferably greater than about 3:1. For sorbitol, the preferred ratio of humectant to water is greater than about 0.5:1, preferably greater than about 1:1.

The inorganic gelling agents incorporated in the dentifrice gel are desirably the amorphous silicas also known as hydrated silicas. Desirably, the hydrated silicas to be used are the hydrogels with a large pore volume of, for example, about 2.5 cc/g (commercially available, for example, as Sylodent 15 and Sylodent 2 from W. R. Grace & Co.). The fumed or pyrogenic silicas (commercially available, for example, as Carbosil from Cabot or Aerosil from Degussa) are equally useful for this application. The advantage of these types of hydrated silicas is that they impart no increased abrasivity to the dentifrice products s formulated. Alternatively or in addition to the inorganic gelling agents, other thickeners conventionally used in dentifrices, such as the natural and synthetic gum-like materials, e.g., Irish Moss, gum tragacanth, sodium CMC, polyvinylpyrrolidone, xanthan gum or starch, may be utilized as thickeners to impart a desirable viscosity and texture to the gel. Most desirably, the thickener is incorporated in an amount of about 0.1 to 1.0% of the formulation.

As recognized by those skilled in the art, additional conventional ingredients, e.g., surfactants, flavoring agents, sweeteners, and fluoridating agents, may be incorporated in the dentifrice gel of the present invention.

Suitable surfactants include anionic surfactants such as the sulfates of long chain ($C_8$–$C_{18}$) alcohols, e.g., sodium lauryl sulfate or sodium tridecylsulfate; the sulfates or sulfonates of monoglycerides, e.g., sodium lauroyl glyceryl sulfate or sodium coconut monoglyceride sulfonate; the sulfonates of succinic esters, e.g., sodium dioctyl sulfosuccinate; the alkyl sulfoacetates such as sodium lauroyl sulfoacetate or sodium coconut sulfoacetate; the salts of sulfoacetic acid modified by aminoethyl long chain fatty acid esters such as sodium sulfocolaurate; the amides formed from higher fatty acids with short chain amino acids such as sodium lauroyl sarcosinate or sodium methyl lauroyl tauride; and soaps such as the sodium, potassium or triethanolamine salts of fatty acids. Similarly, nonionic surfactants may be used such as the ethoxylated sugar esters of the higher fatty acids, for example, ethoxylated sorbitan monostearate and ethoxylated glycerol monostearate. Also, amphoteric surfactants such as the mono or dicarboxylated imidazoline derivatives of fatty acids, e.g., sodium lauryl dicarboxy imidazoline or sodium coconut dicarboxy imidazoline, may be used. Cationic surfactants such as those which additionally impart significant antibacterial action to the gel may also be used in the gel. Examples of such surfactants include benzyl dimethyl stearyl ammonium chloride and cetylpyridinium chloride. Most desirably, the surfactant is incorporated within the range of about 0.2 to 2.0%, by weight of the gel. Flavoring agents useful in the dentifrice gel include the flavoring oils; for example, oils of peppermint, spearmint, menthol, wintergreen, clove, sassafras, cinnamon, lemon, orange, methylsalicylate, licorice, sage, marjoram or eucalyptus. Most desirably, the flavoring agent is present in the gel in an amount within the range of about 0.2 to 2.0% by weight.

Suitable sweeteners include sucrose, lactose, maltose, sorbitol, saccharin, sodium or calcium cyclamate, aspartame, or other sweeteners known to those skilled in the art. The sweetener is most desirably present in the gel in an amount of about 0.1 to 5.0% by weight.

The dentifrice gel of the present invention may additionally contain a fluoridating agent to aid in preventing dental caries. Many fluoridating agents suitable for use in dentifrice compositions are known. Among these are sodium fluoride, potassium fluoride, stannous fluoride or chlorofluoride, potassium stannous fluoride ($Sn_nF_2KF$), and complex fluorides such as sodium fluorozirconate and sodium monofluorophosphate. The fluoridating agent is most desirably present in an amount to provide 1000–2000 ppm fluoride ion in the gel.

Formulation of the gel is completed by the addition of water, most desirably in the amount of about 2 to 10% thereof. As noted previously, higher levels of water reduce the clarity of the dentifrice gel.

The gel may be compounded in any manner known to those in the art, desirably by dissolving the fluoridating agent, sweetener and any colorant in all or part of the water, dispersing the organic thickener into the humectant with high speed stirring (when sorbitol is used the organic thickener; e.g., CMC, is dispersed in a 70% aqueous solution of the humectant), adding the water solution to the humectant and mixing until the solution thickens, adding the bicarbonate and then gradually adding the silica abrasive followed by the silica thickener, adding the flavor and surfactants and mixing while pulling vacuum to remove entrapped air.

The following examples illustrate particularly preferred embodiments of the dentifrice gel of this invention. In the preceding disclosure as well as the following examples, unless otherwise indicated, all parts and percentages are given by weight.

EXAMPLES 1 THROUGH 6 - COMPARISON OF CLARITY OF VARIOUS DENTIFRICE FORMULATIONS

Examples of the sodium bicarbonate-containing dentifrice gels of the invention were prepared (Examples 1–17). The examples were compared as to gel clarity with the following controls:

Controls A–G—commercial dentifrica gels not containing sodium bicarbonate;

Controls H and I —commercial opaque toothpastes; and

Controls J and K —commercial opaque toothpastes containing sodium bicarbonate. The clarity of the various dentifrices was evaluated by placing a 0.2 inch thick film of each formulation onto an 8B Leneta paint test chart by means of a Gardner Microm Film Applicator with adjustable clearance. This test delineates between clear, and partially clear (translucent) gels, and opaque toothpastes. With opaque toothpastes, the black lines on the chart are not visible through the film. However, with translucent gels, the black lines are visible. The results are summarized in Tables I, II, III, IV and V.

TABLE I

Comparison of Clarity of Various Dentifrice Gels of the Invention

| | Example 1 | Example 2 | Example 3 | Example 4 | Example 5 | Example 6 | Example 7 |
|---|---|---|---|---|---|---|---|
| Water | 21.74 | 16.9 | 9.48 | 4.24 | 16.9 | 16.9 | 13.6 |
| Glycerin (100% basis) | — | — | 39.46 | 41.2 | — | — | — |
| Sorbitol (100% basis) | 43.7 | 29.54 | — | — | 29.54 | 29.54 | 23.84 |
| Sylodent 756* | 15.0 | 14.0 | — | 14.0 | 14.0 | 14.0 | — |
| Sylodent 700* | — | — | 14.0 | — | — | — | — |
| Sylodent 15* | 10.0 | 7.0 | 4.5 | 8.0 | 7.0 | 7.0 | — |
| Sodium Bicarbonate (Grade 5) | 7.0 | 30.0 | — | — | — | — | 60.0 |
| Sodium Barcarbonate (Grade 2) | — | — | 30.0 | 30.0 | — | — | — |
| Sodium Bicarbonate (Grade 1) | — | — | — | — | 30.0 | — | — |
| Sodium Bicarbonate (Grade 3DF) | — | — | — | — | — | 30.0 | — |
| Color (Blue #1) | 0.08 | 0.08 | 0.08 | 0.08 | 0.08 | 0.08 | 0.08 |
| Sodium Fluoride | 0.22 | 0.22 | 0.22 | 0.22 | 0.22 | 0.22 | 0.22 |
| Sodium Saccharin | 0.90 | 0.90 | 0.90 | 0.90 | 0.90 | 0.90 | 0.90 |
| CMC | 0.30 | 0.30 | 0.30 | 0.30 | 0.30 | 0.03 | 0.30 |
| Flavor | 0.76 | 0.76 | 0.76 | 0.76 | 0.76 | 0.76 | 0.75 |
| Sodium Lauryl Sulfate | 0.15 | 0.15 | 0.15 | 0.15 | 0.15 | 0.15 | 0.15 |
| Sodium Lauryl Sarcosinate | 0.15 | 0.15 | 0.15 | 0.15 | 0.15 | 0.15 | 0.15 |
| Clarity Rating | 5 | 4 | 3 | 3 | 2 | 1 | 1 |
| Classification | Clear | Almost | Part. | Part. | Border- | Border- | |

TABLE I-continued

Comparison of Clarity of Various Dentrifice Gels of the Invention

| | Example 1 | Example 2 | Example 3 | Example 4 | Example 5 | Example 6 | Example 7 |
|---|---|---|---|---|---|---|---|
| | gel | clear gel | opaque gel | opaque gel | opaque gel | line part. opaque gel | line part. opaque gel |

Clarity Rating System:
0 - Black lines not visible
1 - Black lines barely visible
2 - Black lines visible but not very clear
3 - Black lines visible but only somewhat clear
4 - Black lines visible with very slight haze
5 - Black lines very clear, no haze

*Sylodent 700 and Sylodent 756 are hydrous silica gel abrasives providing moderate and high abrasivity respectively.
Sylodent 15 is a hydrated silica hydrogel of pore volume about 2.5 cc/g. This product is non-abrasive

TABLE II

Comparison of Clarity of Various Dentrifice Gels of the Invention

| | Example 8 | Example 9 | Example 10 | Example 11 |
|---|---|---|---|---|
| Water | 21.29 | 22.04 | 22.04 | 22.04 |
| Sorbitol (100% basis) | 27.54 | 29.29 | 29.29 | 29.29 |
| Sylodent 700* | 14.0 | 10.0 | 8.0 | 6.0 |
| Sylodent 15* | 4.5 | 6.0 | 8.0 | 10.0 |
| Sodium Bicrbonate (Grade 2) | 30.0 | 30.0 | 30.0 | 30.0 |
| Color (Blue #1) | 0.2 | 0.2 | 0.2 | 0.2 |
| Sodium Fluoride | 0.22 | 0.22 | 0.22 | 0.22 |
| Sodium Saccharin | 0.90 | 0.90 | 0.90 | 0.90 |
| CMC | 0.30 | 0.30 | 0.30 | 0.30 |
| Flavor | 0.75 | 0.75 | 0.75 | 0.75 |
| Sodium Lauryl Sulfate | 0.15 | 0.15 | 0.15 | 0.15 |
| Sodium Lauroyl Sarcosinate | 0.15 | 0.15 | 0.15 | 0.15 |
| Clarity Rating | 3 | 3+ | 3 | 2 |
| Classification | Slightly opaque | Slightly opaque | Slightly opaque | Part. opaque |
| | gel | gel | gel | gel |
| Abrasiviy rating (RDA) | 105 | 85 | ·69 | 57 |

*Sylodent 700 is a hydrous silica gel abrasive Sylodent 15 is a hydrated silica hydrogel of pore volume about 2.5 cc/g. This product is non-abrasive.

Clarity Rating System:
0 - Black lines not visible
1 - Black lines barely visible
2 - Black lines visible but not very clear
3 - Black lines visible but only somewhat clear
4 - Black lines visible with very light haze
5 - Black lines very clear, no haze

TABLE III

Comparison of Clarity of Various Dentrifice Gels of the Invention

| | Example 12 | Example 13 | Example 14 | Example 15 | Example 16 |
|---|---|---|---|---|---|
| Water | 16.9 | 21.32 | 20.52 | 24.03 | 26.93 |
| Sorbitol (100% basis) (100% basis) | 29.54 | 27.62 | 24.51 | 21.0 | 16.1 |
| Sylodent 756* | 14.0 | — | 15.0 | 15.0 | 15.0 |
| Sylodent 700* | — | 14.0 | — | — | — |
| Sylodent 15* | 7.0 | 4.5 | 7.0 | 7.0 | 9.0 |
| Sodium Bicarbonate (Grade 2) | 30.0 | 30.0 | 30.0 | 30.0 | 30.0 |
| Color (Blue #1) | 0.08 | 0.08 | 0.20 | 0.20 | 0.20 |
| Sodium Fluoride | 0.22 | 0.22 | 0.22 | 0.22 | 0.22 |
| Sodium Saccharin | 0.90 | 0.90 | 0.90 | 0.90 | 0.90 |
| CMC | 0.30 | 0.30 | 0.60 | 0.60 | 0.60 |
| Flavor | 0.76 | 0.76 | 0.75 | 0.75 | 0.75 |
| Sodium Lauryl Sulfate | 0.15 | 0.15 | 0.15 | 0.15 | 0.15 |
| Sodium Lauroyl Sarcosinate | 0.15 | 0.15 | 0.15 | 0.15 | 0.15 |
| Clarity Rating | 3 | 2 | 2 | 1 | 1 |
| Classification | Slightly opaque gel | Part. opaque gel | Part. opaque gel | Border-line part. opaque gel | Border-line part. opaque gel |

Clarity Rating System:
0 - Black lines not visible
1 - Black lines barely visible
2 - Black lines visible but not very clear
3 - Black lines visible but only somewhat clear
4 - Black line visible with very slight haze
5 - Black lines very clear, no haze

*Sylodent 700 and Sylodent 756 are hydrous silica gel abrasives providing moderate and high abrasivity respectively. Sylodent 15 is a hydrated silica hydrogel of pore volume about 2.5 cc/g. This product is non-abrasive.

TABLE IV

Comparison of Clarity of Various Dentifrice Gels of the Invention

|  | Example 17 | Example 18 | Example 19 |
|---|---|---|---|
| Water | 17.41 | 19.24 | 19.48 |
| Sorbitol (100% basis) | 33.61 | 39.0 | 38.0 |
| Polyethylene glycol (400 MW) | 5.0 | — | — |
| Ethyl alcohol | 2.0 | — | — |
| Sylodent 756* | 15.0 | 15.0 | 15.0 |
| Sylodent 15* | 9.0 | 9.0 | 9.0 |
| Sodium bicarbonate (Grade 5) | 15.0 | 15.0 | 15.0 |
| Color (blue #1) | 0.2 | — | — |
| Sodium monofluorophophate | — | — | 0.76 |
| Sodium fluoride | 0.22 | — | — |
| Sodium saccharin | 0.9 | 0.9 | 0.9 |
| CMC | 0.6 | 0.6 | 0.6 |
| Flavor | 0.76 | 0.76 | 0.76 |
| Sodium lauryl sulfate | 0.15 | 0.50 | 0.50 |
| Sodium lauroyl sarcosinate | 0.15 | — | — |
| Clarity rating | 4 | | |
| Classification | Almost clear gel | | |

*Sylodnt 756 is a hydrous silica gel abrasive. Sylodent 15 is a non-abrasive hydrated silica hydrogel of pore volume 2.5 cc/g.

feasibly be incorporated into a dentifrice while retaining some degree of translucency. The resulting partially opaque gel has an interesting granular crystalline appearance.

When very fine grades of sodium bicarbonate were used, significantly less bicarbonate could be incorporated into the product without the loss of gel characteristics. For example, when grade 3DF (bicarbonate of median particle size of less than 44 microns) was used (Example 6) only 30% sodium bicarbonate could be incorporated into the formulation while maintaining the characteristics of a partially opaque gel. The resulting product has an extremely smooth appearance.

Formulations containing grade 1 (sodium bicarbonate of median particle size in the range of from 44 to 74 —Example 5) and grade 2 (sodium bicarbonate of median particle size within the range of from 74 to 149 microns —Examples 3 and 4) also provide partially clear gels when 30% sodium bicarbonate is incorporated into the formulation. These products have significantly higher clarity than the previous two products. Indeed, comparison of Examples 2, 3, 4, 5 and 6 illustrate the effects on clarity of reducing the particle size of the bicarbonate used. In each of these examples, 30% bicarbonate was used and the effect of reducing particle size was to systematically reduce the clarity rating from 4 to 1. Examination of these products also shows that the texture o these products becomes systematically less granular as the bicarbonate particle size is reduced.

Utilizing a coarse grade of sodium bicarbonate (Grade 5, of median particle size between 149 and 210 microns) at a low level (7%) allows a completely clear gel to be prepared (Example 1). This product also has a slightly granular texture.

TABLE V

Comparison of Clarity of Various Control Dentifrice Formulations

|  | Control A "Aim" | Control B "Colgate Gel" | Control C "Crest Gel" | Control D "Topol Gel" | Control E "Check-Up Gel" | Control F "Colgate Tartar Control Gel" | Control G "Crest Tartar Control Gel" | Control H "Crest Tartar Control Paste" | Control I "Colgate Dental Cream" | Control J "Colgate Peak* Tooth Paste" | Control K "Arm & Hammer** Dental Care Tooth Paste" |
|---|---|---|---|---|---|---|---|---|---|---|---|
| Sorbitol | + | + | + | + | + | + | + | + | — | — | — |
| Glycerin | — | + | — | + | + | + | + | — | + | + | + |
| Polyethylene glycol | + | + | — | — | + | + | + | — | — | — | + |
| Water | + | + | + | + | + | + | + | + | + | + | + |
| Hydrated silica | + | + | + | + | + | + | + | + | — | + | — |
| Dicalcium phosphate | — | — | — | + | — | — | — | — | — | — | — |
| Dicalium phosphate dihydrate | — | — | — | — | — | — | — | — | + | — | — |
| Aluminum silicate | — | — | — | + | — | — | — | — | — | + | — |
| Alumina | — | — | — | + | — | — | — | — | — | + | — |
| Calcium carbonate | — | — | — | — | — | — | — | — | — | + | — |
| Sodium bicarbonate | — | — | — | — | — | — | — | + | — | + | + |
| Flavor/Saccharin | + | + | + | + | + | + | + | + | + | + | + |
| Organic thickener such as CMC, xanthangum, carrageenan, etc. | + | + | + | + | + | + | + | — | + | — | + |
| Sodium monofluorophosphate | + | + | — | — | — | — | — | — | + | — | — |
| Sodium fluoride | — | — | + | + | + | + | + | + | — | — | + |
| Sodium lauryl sulfate | + | + | + | + | + | + | + | + | + | + | + |
| Sodium lauroyl sarcosinate | — | — | — | — | — | — | — | — | — | — | + |
| Sodium pyrophosphate | — | — | — | — | — | + | + | + | + | — | — |
| Other | + | + | + | + | + | + | + | + | + | + | + |
| Clarity rating | 5 | 4 | 4 | 4 | 5 | 1 | 3 | 0 | 0 | 0 | 0 |

**Contains about 65% NaHCO₃
*Contains about 38% NaHCO₃

The above data exemplify the translucent sodium bicarbonate-containing dentifrice gels of the invention. A gel containing 60% sodium bicarbonate was prepared when a coarse grade (Grade 5, having median particle size in the range of from 149 to 210 microns) of sodium bicarbonate was used, viz., Example 7. This example illustrates the highest level of bicarbonate which can An almost clear gel is produced when 15% grade 5 (median particle size between 149 and 210 microns) is utilized (Example 17).

Comparison of Examples 8, 9, 10 and 11 show the flexibility in abrasivity characteristics available by varying the level of hydrated silica abrasive (Sylodent 700). In these formulations, the level of silica thickener (Sylodent 15) was adjusted to maintain comparable viscosity between the formulations. It can be seen that these changes in level of abrasive and thickener had only a minor effect on product clarity.

A change in abrasivity characteristics can also be accomplished by changing the hydrated silica abrasive. The use of Sylodent 756 results in much higher abrasivity. Thus, Example 2 using 14% Sylodent 756 was found to have an abrasivity value (RDA) of 156.

The effect of humectant to water ratio on product clarity is illustrated in Examples 12, 13, 14, 15 and 16. It can be seen that increasing the level of water and reducing the humectant (Sorbitol) has a detrimental effect on product clarity. Example 16 illustrates the approximately highest level of water and lowest level of humectant desirable for a product containing 30% grade 2 sodium bicarbonate (of median particle size between 74 and 149 microns) while maintaining the characteristics of a gel. Comparison of Example 12 with Example 4 shows that formulations containing sorbitol as the humectant retain gel clarity at higher levels of water than formulations utilizing glycerin.

Example 17 illustrates the ability to use polyethylene glycol and ethanol in the formulation while producing a gel dentifrice of the invention.

Example 18 illustrates a gel formulation of the invention with no fluoride. Example 19 illustrates a gel formulation of the invention utilizing a desirable level of sodium monofluorophosphate.

It will be understood that the preferred dentifrice gel compositions of the invention described herein are illustrative only, and should not be construed as limiting the present invention.

What is claimed is:

1. A dentifrice gel comprising a sodium bicarbonate abrasive in an aqueous carrier, the sodium bicarbonate having a median particle size range of from 10 to 200 microns and being incorporated in the gel in an amount of from 5 to 60% by weight of the gel, and the carrier incorporating a humectant selected from the group consisting of glycerin, sorbitol, a low molecular weight polyethylene glycol, propylene glycol, and mixtures thereof in an amount of from 15 to 60% by weight of the gel and in at least a 0.5:1 ratio relative to the water content thereof.

2. The dentifrice gel of claim 1 further comprising up to 20% by weight of a secondary abrasive selected from the group consisting of hydrous silica gels, alkali metal phosphates and complex aluminosilicates.

3. The gel of claim 1, further comprising up to 3% by weight of a thickener selected from the group consisting of silica thickeners and natural and synthetic gum-like materials.

4. The gel of claim 1, further comprising up to 5% by weight of a surfactant.

5. The dentifrice gel of claim 1, further comprising up to 2% by weight of a flavoring agent.

6. The dentifrice gel of claim 1, further comprising up to 5% by weight of a sweetener.

7. The dentifrice gel of claim 1, further comprising up to 3% by weight of a fluoridating agent.

8. A sodium bicarbonate-based dentifrice gel exhibiting optical translucence, which comprises:

| Ingredient | % by Weight |
| --- | --- |
| sodium bicarbonate (median particle size from 10 to 200 microns) | 5 to 60% |
| humectant | 15 to 60% |
| thickener | 0.1 to 1.0% |
| surfactant | 0.2 to 2.0% |
| flavoring agent | 0.2 to 2.0% |
| sweetener | 0.1 to 5.0% |
| water | 2 to 10% |

9. The sodium bicarbonate-based dentifrice gel of claim 8, further comprising from 5 to 15% by weight of a secondary abrasive selected from the group consisting of hydrous silica gels, alkali metal phosphates and complex aluminosilicates.

10. A sodium bicarbonate-based dentifrice gel exhibiting optical translucence, comprising:
 (a) from 15 to 35% by weight of a sodium bicarbonate abrasive having particle sizes from 74 to 149 microns;
 (b) from 5 to 15% by weight of a secondary abrasive selected from the group consisting of hydrous silica gels, alkali metal phosphates and complex aluminosilicates;
 (c) from 15 to 60% by weight of a humectant selected from the group consisting of glycerin, sorbitol, a low molecular weight polyethylene glycol, propylene glycol, and mixtures thereof;
 (d) from 0.1 to 1.0% by weight of a thickener selected from the group consisting of silica thickeners and natural and synthetic gum-like materials;
 (e) from 0.2 to 2.0% by weight of a surfactant;
 (f) from 0.2 to 2.0% by weight of a flavoring agent;
 (g) from 0.1 to 5.0% by weight of a sweetener; and
 (h) from 2.0 to 10.0% by weight water.

11. The dentifrice gel of claim 10, further comprising a fluoridating agent in an amount sufficient to provide 1000–2000 ppm fluoride ion in the gel.

12. The dentifrice gel of claim 1 wherein the sodium bicarbonate median particle size range is from 44 to 200 microns and is incorporated in the gel in an amount of from 5 to 50% by weight of the gel, and wherein the humectant is incorporated in at least a 1:1 ratio relative to the water content thereof.

* * * * *